United States Patent
Kashima

(10) Patent No.: US 10,701,339 B2
(45) Date of Patent: Jun. 30, 2020

(54) IMAGE PROCESSING DEVICE AND IMAGE PROCESSING METHOD

(71) Applicant: SONY CORPORATION, Tokyo (JP)

(72) Inventor: Koji Kashima, Kanagawa (JP)

(73) Assignee: SONY CORPORATION, Tokyo (JP)

( * ) Notice: Subject to any disclaimer, the term of this patent is extended or adjusted under 35 U.S.C. 154(b) by 169 days.

(21) Appl. No.: 15/510,124

(22) PCT Filed: Sep. 4, 2015

(86) PCT No.: PCT/JP2015/075161
§ 371 (c)(1),
(2) Date: Mar. 9, 2017

(87) PCT Pub. No.: WO2016/043063
PCT Pub. Date: Mar. 24, 2016

(65) Prior Publication Data
US 2017/0257619 A1   Sep. 7, 2017

(30) Foreign Application Priority Data

Sep. 18, 2014 (JP) .................... 2014-190164

(51) Int. Cl.
*H04N 13/00* (2018.01)
*A61B 1/06* (2006.01)
(Continued)

(52) U.S. Cl.
CPC ....... *H04N 13/239* (2018.05); *A61B 1/00009* (2013.01); *A61B 1/00045* (2013.01);
(Continued)

(58) Field of Classification Search
CPC ............ A61B 1/00009; A61B 1/00181; A61B 1/00091; A61B 1/00096; A61B 1/00174;
(Continued)

(56) References Cited

U.S. PATENT DOCUMENTS

2005/0197533 A1* 9/2005 May .................... A61B 1/00071
600/164
2013/0076879 A1* 3/2013 On ..................... A61B 1/00009
348/65
(Continued)

FOREIGN PATENT DOCUMENTS

CN    103841879 A    6/2014
CN    104853665 A    8/2015
(Continued)

OTHER PUBLICATIONS

International Search Report and Written Opinion of PCT Application No. PCT/JP2015/075161, dated Dec. 1, 2015, 06 pages of English Translation and 06 pages of ISRWO.
(Continued)

*Primary Examiner* — Mulugeta Mengesha
*Assistant Examiner* — Alazar Tilahun
(74) *Attorney, Agent, or Firm* — Xsensus LLP

(57) ABSTRACT

The present disclosure relates to an image processing device and an image processing method that can present an image that is obtained by a front view camera and a side view camera in an easily comprehensible manner. Provided is an image processing device including: an image combining unit configured to generate a combined image in which a front view image that is obtained by capturing an image of a subject in a front view direction which is a distal end direction of a probe is located in a region of a circular shape, and a side view image that is obtained by capturing an image of a subject in a side view direction which is a side direction of the probe is located in a fan shape along an outer circumference of the circular shape. The present disclosure can be applied to, for example, an image processing device.

20 Claims, 16 Drawing Sheets

(51) Int. Cl.
*A61B 1/045* (2006.01)
*A61B 1/05* (2006.01)
*H04N 13/239* (2018.01)
*A61B 1/04* (2006.01)
*H04N 5/247* (2006.01)
*A61B 1/00* (2006.01)
*H04N 13/156* (2018.01)
*H04N 5/225* (2006.01)

(52) U.S. Cl.
CPC ............ *A61B 1/00188* (2013.01); *A61B 1/04* (2013.01); *A61B 1/045* (2013.01); *A61B 1/051* (2013.01); *A61B 1/06* (2013.01); *H04N 5/247* (2013.01); *H04N 13/156* (2018.05); *H04N 2005/2255* (2013.01)

(58) Field of Classification Search
CPC ..... A61B 1/00177; A61B 1/015; A61B 1/051; A61B 1/0676; A61B 1/126; A61B 1/00188; A61B 1/045; A61B 1/00045; A61B 1/06; A61B 1/04; G02B 23/2423; G02B 23/243; G06T 2207/10068; H04N 13/239; H04N 5/247; H04N 13/156; H04N 2005/2255
See application file for complete search history.

(56) References Cited

U.S. PATENT DOCUMENTS

| 2014/0204187 | A1  | 7/2014  | Sasaki et al. |
| 2014/0350338 | A1* | 11/2014 | Tanaka ............... A61B 1/00009 600/111 |
| 2015/0265136 | A1* | 9/2015  | Honda ................. A61B 1/051 600/157 |
| 2016/0006943 | A1* | 1/2016  | Ratnakar ............ A61B 1/00009 348/36 |

FOREIGN PATENT DOCUMENTS

| EP | 2762059 A1 | 8/2014 |
| EP | 2929830 A1 | 10/2015 |
| JP | 2010-279539 A | 12/2010 |
| JP | 2013-66646 A | 4/2013 |
| JP | 2013-66648 A | 4/2013 |
| WO | 2014/88076 A1 | 6/2014 |

OTHER PUBLICATIONS

International Preliminary Report on Patentability of PCT Application No. PCT/JP2015/075161, dated Mar. 30, 2017, 07 pages of English Translation and 03 pages of IPRP.

* cited by examiner

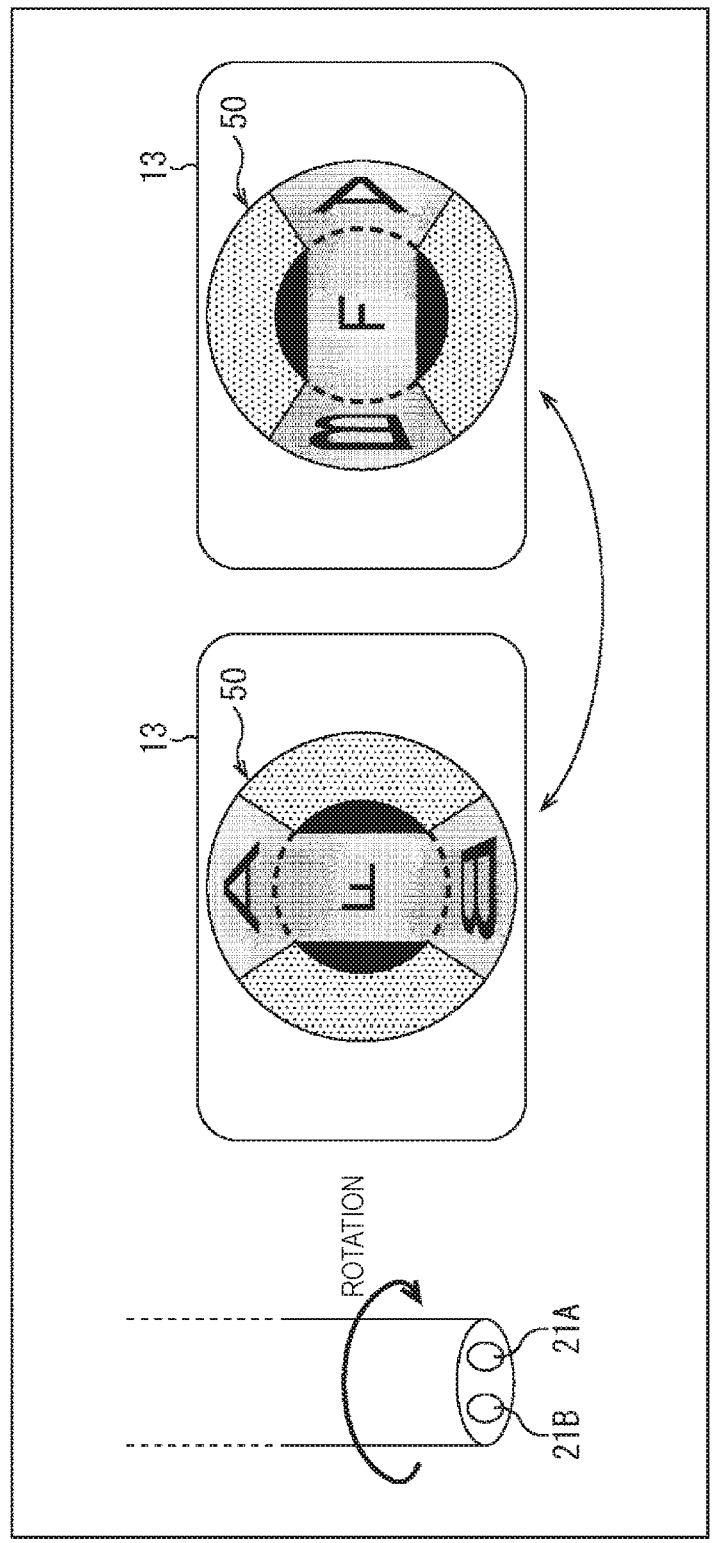

IMAGE PROCESSING DEVICE AND IMAGE PROCESSING METHOD

CROSS REFERENCE TO RELATED APPLICATIONS

This application is a U.S. National Phase of International Patent Application No. PCT/JP2015/075161 filed on Sep. 4, 2014, which claims priority benefit of Japanese Patent Application No. JP 2014-190164 filed in the Japan Patent Office on Sep. 18, 2014. Each of the above-referenced applications is hereby incorporated herein by reference in its entirety.

TECHNICAL FIELD

The present disclosure relates to an image processing device and an image processing method, and particularly relates to an image processing device and an image processing method that can present an image that is obtained by a front view camera and a side view camera in an easily comprehensible manner.

BACKGROUND ART

There is proposed an endoscope probe that is used in endoscopic surgical operation and includes a front view camera that captures an image of a front view direction which is a distal end direction of the probe as well as a side view camera that captures an image of a side view direction which is a side direction of the probe (for example, refer to Patent Literatures 1 and 2).

CITATION LIST

Patent Literature

Patent Literature 1: JP 2012-120621A
Patent Literature 2: WO 2012/77117

DISCLOSURE OF INVENTION

Technical Problem

The side view camera enables enlargement of a view field other than an operative field in the front view direction, but images that are obtained by the front view camera and the side view camera are required to be presented in an easily comprehensible manner for a surgeon.

The present disclosure is made in view of the above situation, and presents the images that are obtained by the front view camera and the side view camera in an easily comprehensible manner.

Solution to Problem

According to an aspect of the present disclosure, there is provided an image processing device including: an image combining unit configured to generate a combined image in which a front view image that is obtained by capturing an image of a subject in a front view direction which is a distal end direction of a probe is located in a region of a circular shape, and a side view image that is obtained by capturing an image of a subject in a side view direction which is a side direction of the probe is located in a fan shape along an outer circumference of the circular shape.

According to an aspect of the present disclosure, there is provided an image processing method including: generating, by an image processing device, a combined image in which a front view image that is obtained by capturing an image of a subject in a front view direction which is a distal end direction of a probe is located in a region of a circular shape, and a side view image that is obtained by capturing an image of a subject in a side view direction which is a side direction of the probe is located in a fan shape along an outer circumference of the circular shape.

In an aspect of the present disclosure, a combined image is generated in which a front view image that is obtained by capturing an image of a subject in a front view direction which is a distal end direction of a probe is located in a region of a circular shape, and a side view image that is obtained by capturing an image of a subject in a side view direction which is a side direction of the probe is located in a fan shape along an outer circumference of the circular shape.

The image processing device may be an independent device or may be an internal block constituting a single device.

Advantageous Effects of Invention

According to one aspect of the present disclosure, the images that are obtained by the front view camera and the side view camera can be presented in an easily comprehensible manner.

Note that the effect described herein is not necessarily limited and may be any one of effects described in the present disclosure.

BRIEF DESCRIPTION OF DRAWINGS

FIG. 7 is a diagram for describing a display of a combined image.

MODE(S) FOR CARRYING OUT THE INVENTION

<Exemplary Configuration of Endoscope System>

Figure 1:
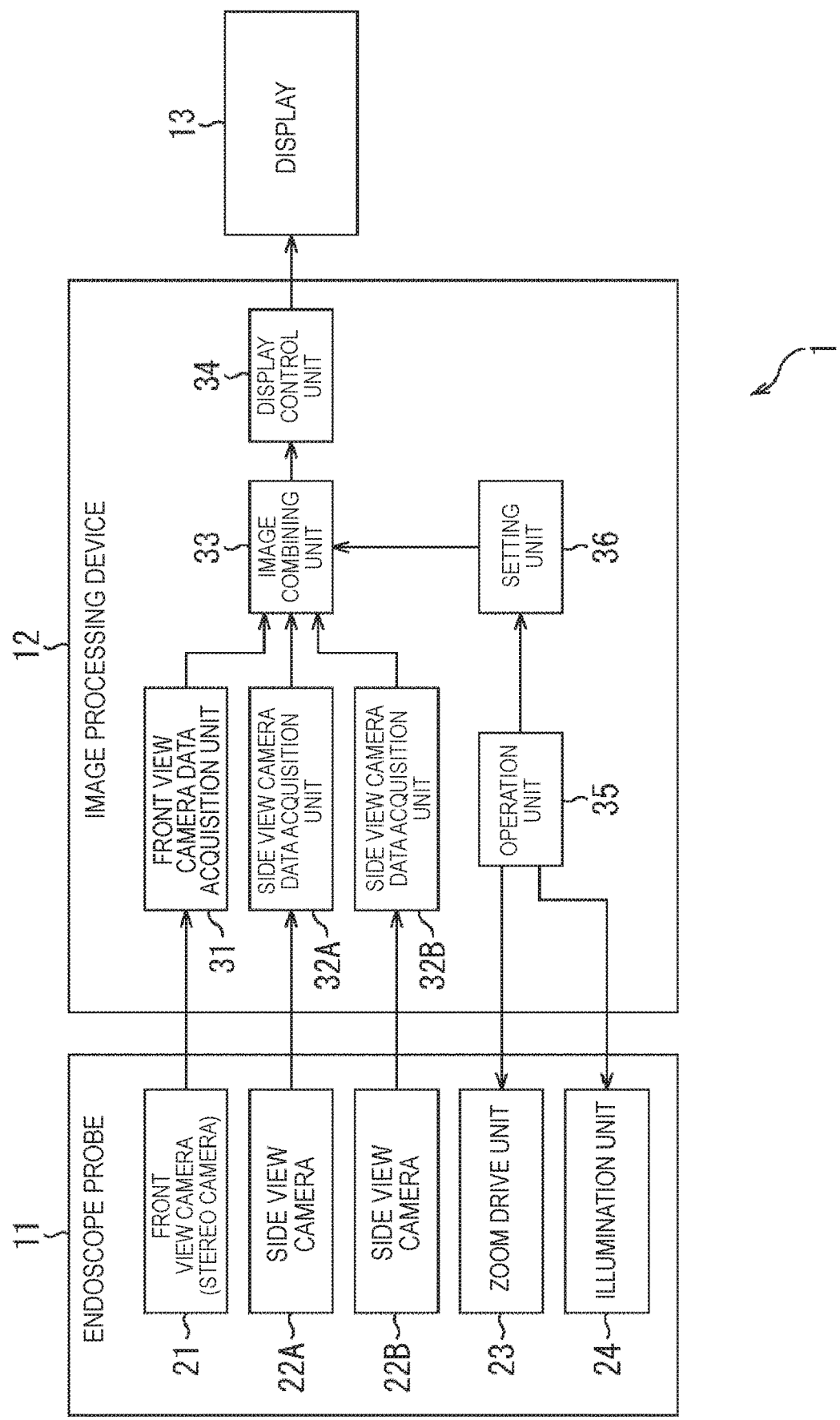
FIG. 1 is a block diagram illustrating an exemplary configuration of one embodiment of an endoscope system according to the present disclosure.

FIG. 1 is a block diagram illustrating an exemplary configuration of one embodiment of an endoscope system according to the present disclosure.

The endoscope system 1 of FIG. 1 is configured with an endoscope probe 11, an image processing device 12, and a display 13.

The endoscope system 1 is used in an endoscopic surgical operation that captures an image of a portion (a surgical site) inside a body of a surgical operation target as an observed portion, and displays the captured image on a display 13, and performs operation to the observed portion while the display 13 is viewed.

The endoscope probe 11 is inserted into an inside of a body of a patient, and captures an image of the surgical site by radiating light at the surgical site, and supplies the captured image to the image processing device 12. The image processing device 12 processes (image processing) the image that is captured by the endoscope probe 11, so that a surgeon can view the image easily. The display 13 displays the image after processing that is supplied from the image processing device 12, in order to present the image to the surgeon.

The endoscope probe 11 includes a front view camera 21, a side view cameras 22A and 22B, a zoom drive unit 23, and an illumination unit 24.

The image processing device 12 includes a front view camera data acquisition unit 31, side view camera data acquisition units 32A and 32B, an image combining unit 33, a display control unit 34, an operation unit 35, and a setting unit 36.

The front view camera 21 captures an image of a subject in a front view direction which is a distal end direction of the endoscope probe 11, and generates an image obtained as the result. The side view cameras 22A and 22B capture images of the subject in side view directions which are side directions of the endoscope probe 11, and generates images obtained as the result. The front view camera 21 and the side view cameras 22A and 22B are configured with image sensors, such as a charge coupled device (CCD) and a complementary metal oxide semiconductor (CMOS) sensor, for example.

Figure 2:
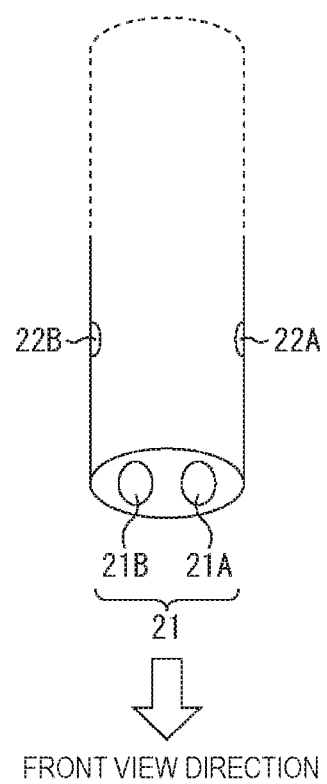
FIG. 2 is a diagram illustrating a distal end part of an endoscope probe.

FIG. 2 is a diagram illustrating a distal end part of the endoscope probe 11 in which the front view camera 21 and the side view cameras 22A and 22B are provided.

As illustrated in FIG. 2, the front view camera 21 is configured with stereo cameras including a first camera 21A and a second camera 21B, and is attached to the distal end of the endoscope probe 11, so that the front view direction of the endoscope probe 11 is aligned with an image capturing direction.

Also, the side view cameras 22A and 22B are attached to symmetric positions with regard to the shaft center of the endoscope probe 11, on a cylindrical side surface within a predetermined distance from the distal end of the endoscope probe 11, so that image capturing scopes are equal.

The front view camera 21 capture an image of the surgical site, whereas the side view cameras 22A and 22B capture images of an portion surrounding the surgical site as auxiliary information. Thus, for example, the front view camera 21 and the side view cameras 22A and 22B can be image sensors of different resolutions, in such a manner that the front view camera 21 employs an image sensor of high resolution in which the number of pixels in the horizontal direction×the vertical direction is approximately 4000×approximately 2000, which is called 4K camera, and each of the side view cameras 22A and 22B employs an image sensor of low resolution in which the number of pixels in the horizontal direction×the vertical direction is approximately 2000×approximately 1000.

Note that, in the present embodiment, the front view camera 21 and the side view cameras 22A and 22B are of a Chip-On-Tip type in which image sensors are attached to a distal end portion of the endoscope probe 11, but may have a structure in which the image sensors are located at a camera control unit (CCU) or the like at a root of the endoscope probe 11 so that light is taken inside at the distal end portion of the endoscope probe 11 and is transmitted to the image sensors, via an optical fiber or the like.

Returning to FIG. 1, the zoom drive unit 23 drives an optical lens of an imaging optical system, on the basis of a control signal that is supplied from the operation unit 35 of the image processing device 12. Thereby, focus and zoom magnification of the front view camera 21 displayed on the display 13 are changed. Note that, in the present embodiment, zoom magnifications of the side view cameras 22A and 22B are fixed, but the zoom magnifications of the side view cameras 22A and 22B may be changeable in the same way as the front view camera 21.

The illumination unit 24 is configured with a halogen lamp, a xenon lamp, a light emitting diode (LED) light source, or the like, for example, and emits light for lighting the surgical site. For example, the illumination unit 24 can be configured in such a manner that a LED light source is located at the vicinity of the of each of the front view camera 21 and the side view cameras 22A and 22B of FIG. 2, and may be configured in such a manner that only a light emission unit is provided at the vicinity of each of the front view camera 21 and the side view cameras 22A and 22B so that light from a light source unit, such as a halogen lamp and a xenon lamp, is transmitted to the emission unit via an optical fiber or the like and output. Turning on and off and the light amount of illumination of the illumination unit 24 are controlled by a control signal from the operation unit 35.

The front view camera data acquisition unit 31 acquires captured image data obtained by the front view camera 21, and supplies the captured image data to the image combining unit 33.

The side view camera data acquisition unit 32A acquires captured image data obtained by the side view camera 22A, and supplies the captured image data to the image combining unit 33. The side view camera data acquisition unit 32B acquires captured image data obtained by the side view camera 22B, and supplies the captured image data to the image combining unit 33.

The image combining unit 33 generates a combined image in which the captured images obtained by the front view camera 21, the side view camera 22A, and the side view camera 22B are located at predetermined positions, and supplies the combined image to the display control unit 34. The parameters are supplied from the setting unit 36 to the image combining unit 33, and the image combining unit 33 generates the combined image according to the parameters. The detail of the combined image generated by the image combining unit 33 will be described later.

The display control unit 34 converts the image data of the combined image supplied from the image combining unit 33 to an image signal of an input format of the display 13 and outputs the image signal to the display 13, in order to display the combined image on the display 13.

The display 13 is configured with a liquid crystal display (LCD) or the like for example, and enables 2D display and 3D display corresponding to stereo camera. As a matter of course, when 3D display is unnecessary, the display 13 can be a display that is capable of 2D display only. Also, the display 13 may be a head-mounted display or the like.

The operation unit 35 accepts operation of a surgeon (user) to the endoscope probe 11, such as the zoom magnification and the illumination light amount, and outputs a control signal to the zoom drive unit 23 and the illumination unit 24, according to the accepted operation detail.

Also, the operation unit 35 accepts an input of the parameters for generating the combined image and outputs the input parameters to the setting unit 36.

The setting unit 36 acquires various types of parameters that are supplied from the operation unit 35, and saves the parameters in an internal memory. Also, the setting unit 36 supplies various types of parameter stored in the memory, to the image combining unit 33 as necessary.

The endoscope system 1 is configured as above.

<Description of Combined Image>

Figure 3:
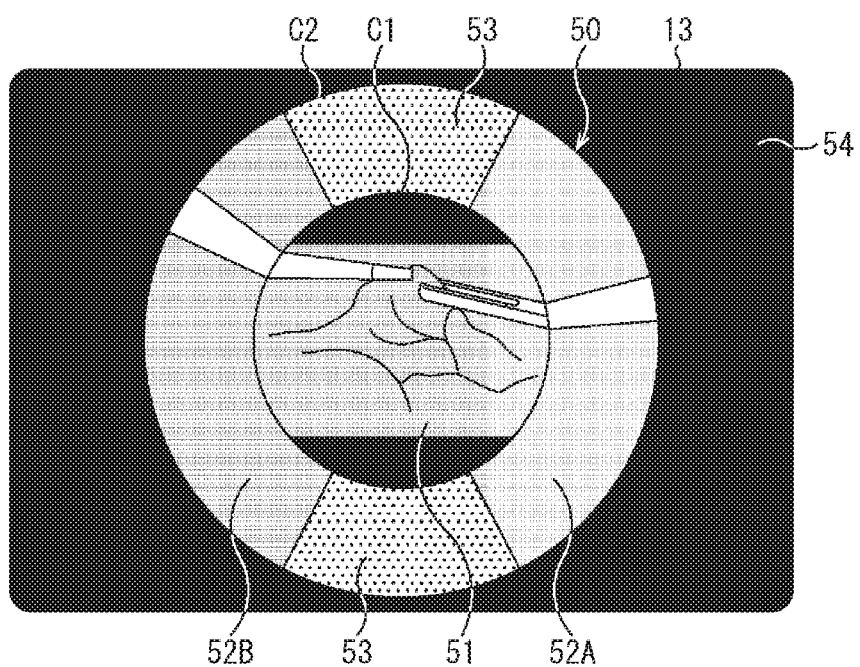
FIG. 3 is a diagram illustrating an example of a combined image displayed on a display.

FIG. 3 illustrates an example of the combined image generated by the image combining unit 33 and displayed on the display 13.

The combined image 50 includes a first circle C1 and a second circle C2 of a larger diameter than the first circle C1. A front view image display region 51 is provided inside the first circle C1. The front view image display region 51 is a region in which an image that is captured by the front view camera 21 is displayed. In the following, the image that is captured by the front view camera 21 is also referred to as a front view image.

Also, a side view A camera display region 52A and a side view B camera display region 52B are provided in a region between the first circle C1 and the second circle C2. The side view A camera display region 52A is a region in which the image that is captured by the side view camera 22A is displayed, and the side view B camera display region 52B is a region in which the image that is captured by the side view camera 22B is displayed.

Each of the side view A camera display region 52A and the side view B camera display region 52B has a fan shape. Also, the side view A camera display region 52A and the side view B camera display region 52B are located at symmetric positions corresponding to the positions of the side view cameras 22A and 22B. In the following, the image that is captured by the side view camera 22A or 22B is also referred to as a side view image. Also, when each of the side view cameras 22A and 22B is needless to be distinguished, each of the side view cameras 22A and 22B is simply referred to as a side view camera 22.

A process for converting a rectangular side view image that is obtained by the side view camera 22 to a fan shape can employ a scan conversion process which is used in an algorithm of B mode display that uses a convex array probe of an ultrasonic diagnostic apparatus. The scan conversion process is a process that converts image data expressed by a signal sequence of scanning line to image data expressed by an orthogonal coordinate system. The data is sparser when getting closer to the outside of the fan shape, and thus the data is appropriately interpolated by using linear interpolation or the like. The detail of the scan conversion process is disclosed in "http://www.cse.wustl.edu/~jain/cse567-08/ftp/scan/", "http://ece.gmu.edu/~ssikdar/papers/conference %20papers/Sikdar_SPIE_2001.pdf", "http://www.ti.com/lit/an/sprab32/sprab32.pdf", for example.

An undisplayed region 53 other than the side view A camera display region 52A and the side view B camera display region 52B in the region between the first circle C1 and the second circle C2 is a region in which the image that is captured by the side view camera 22 is not displayed. The undisplayed region 53 is a display, such as a gray display, from which the surgeon can clearly recognize that there is no displayed image.

For example, parameter information, such as zoom magnification, is displayed in a region 54 outside the combined image 50, in the display region of the display 13.

As described above, the image processing device 12 generates a combined image in which the front view image captured by the front view camera 21 is located in the circular region of the first circle C1 at the inside and the side view images captured by the side view cameras 22A and 22B are located in fan shapes along the outer circumference of the first circle C1, and displays the combined image on the display 13.

In recent years, the surgical operation display 13 tends to have a higher definition and a larger screen. As described above, the display area of the display 13 can be utilized effectively by presenting the side view images as additional information on the circumference of the front view image.

A positional relationship between the front view image and the side view images in the combined image will be described with reference to FIGS. 4A and 4B and FIG. 5.

Figure 4A:
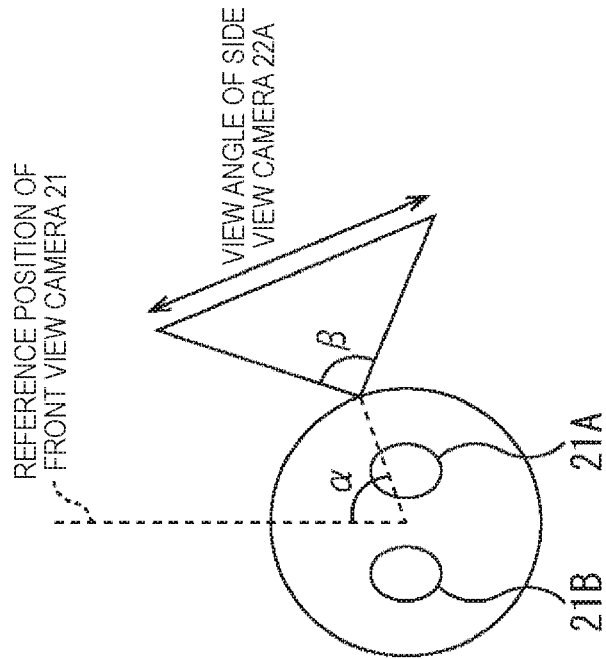
FIGS. 4A and 4B are diagrams for describing a positional relationship of a front view image and a side view image.
Figure 4B:
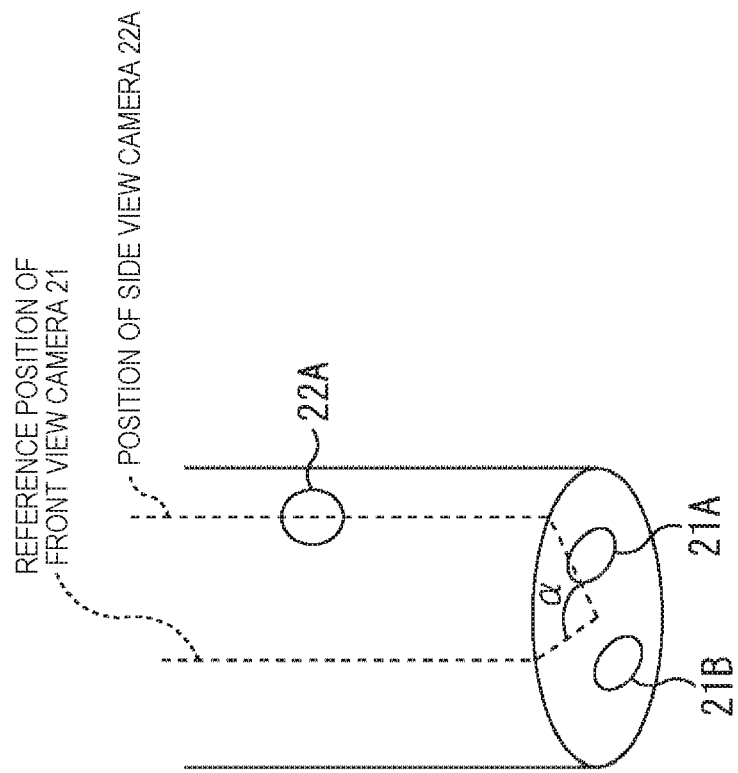

FIG. 4A is a perspective view of the distal end part of the endoscope probe 11 seen from the obliquely downward direction, and FIG. 4B is a diagram of the distal end part of the endoscope probe 11 seen from directly below.

When a predetermined position (direction) of the front view camera 21 is set as a reference position (a reference direction), the position (direction) at which the side view camera 22A is located is set uniquely at a predetermined angle α in relation to the reference position of the front view camera 21, as illustrated in FIG. 4A.

Also, a view angle β of the side view camera 22A illustrated in FIG. 4B is set uniquely by lens design.

Figure 5:
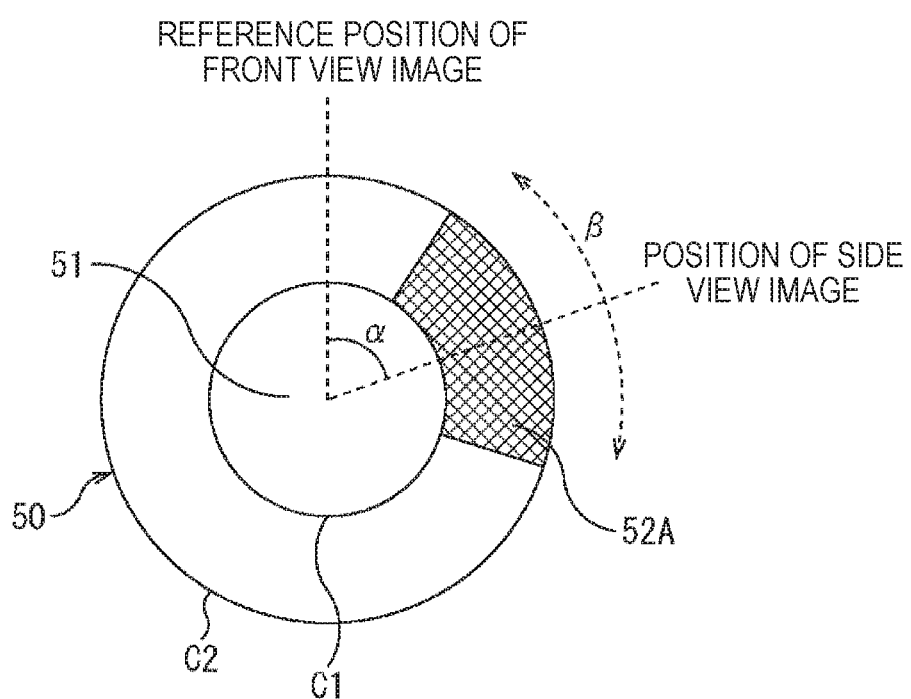
FIG. 5 is a diagram for describing a positional relationship of a front view image and a side view image.
Figure 6A:
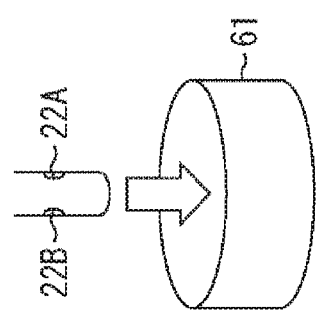
FIGS. 6A, 6B and 6C are diagrams for describing a display of a combined image.
Figure 6B:
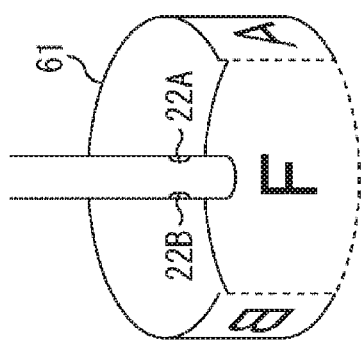
Figure 6C:
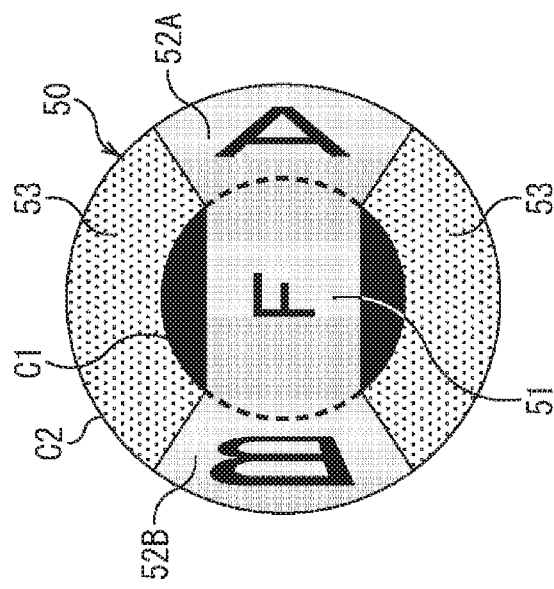

The side view A camera display region 52A in the combined image is decided at a predetermined position in the region between the first circle C1 and the second circle C2, as illustrated in FIG. 5, on the basis of the location angle α and the view angle β of the side view camera 22A. That is, the side view A camera display region 52A is located at the region between the first circle C1 and the second circle C2, in such a manner that the center position in the circular arc direction of the side view A camera display region 52A is at the position of angle α in relation to the reference position of the front view image and that the angle of the fan shape of the side view A camera display region 52A is β. The positional relationship of the side view B camera display region 52B to the front view image display region 51 is likewise. Thereby, the combined image is displayed so as to ensure video continuity of the front view image and the side view image, and visibility of the operative field of the surgeon is improved.

Note that, when the image sensor is not the Chip-On-Tip type in which the image sensor is attached to the distal end portion of the endoscope probe 11, but the positional relationship between the direction of the image sensor and the direction of the distal end part of the endoscope probe 11 can change, the location of the side view A camera display region 52A can be decided by providing a cutout indicating the reference position (reference direction) of the front view camera 21 at the distal end part of the endoscope probe 11 so that the cutout appears in the front view image, detecting the cutout in the front view image by image processing to detect the direction of the front view camera 21, and calculating the angle α of the side view camera 22A on the basis of the detected direction, for example.

Next, display of the combined image will be described, with reference to FIGS. 6A, 6B, and 6C and FIG. 7.

The space inside the body into which the endoscope probe 11 is inserted is assumed as a space inside a cylindrical shape 61, as illustrated in FIG. 6 A. For example, character "F" is written on a bottom surface of the cylindrical shape 61, and character "A" and character "B" are written at opposite positions on an inside surface (inner wall) of the cylindrical shape 61, as illustrated in FIG. 6 B.

In this case, the combined image 50 illustrated in FIG. 6 C is generated, by the image combining unit 33 of the image processing device 12. That is, the character "F" is displayed in the front view image display region 51 of the combined image 50, and the character "A" is displayed in the side view A camera display region 52A, and the character "B" is displayed in the side view B camera display region 52B.

Also, as illustrated in FIG. 7, when the endoscope probe 11 is rotated by the operation of the surgeon, the display of the combined image 50 of the display 13 can be rotated according to the motion of the endoscope probe 11. Alternatively, the display of the combined image 50 may be fixed, regardless of the motion of the endoscope probe 11.

The 3D image captured by the binocular front view camera 21 is displayed in the front view image display region 51. Here, the 3D image is 2D images for performing 3D display, and is composed of a set of a left eye image and a right eye image. Parallax is set in the left eye image and the right eye image, and a person who views the displayed video is caused to perceive stereoscopic effect (depth effect), by displaying the left eye image and the right eye image alternatingly.

On the other hand, the flat images (2D images) obtained by the corresponding monocular side view cameras 22 (22A and 22B) are displayed in the side view A camera display region 52A and the side view B camera display region 52B.

Alternatively, the image combining unit 33 may generate the left eye image and the right eye image that include the parallax, from the images that are obtained by the corresponding monocular side view cameras 22, also with regard to the side view A camera display region 52A and the side view B camera display region 52B, in order to display the 3D image. In this case, as a position (a coordinate point) in the side view A camera display region 52A and the side view B camera display region 52B is farther from the front view image display region 51, in other words, is close to the outside of the fan shape, a generated stereoscopic image has less depth effect and causes a feeling of being nearer.

A display viewed when peering into the surgical site from above the surgical site is enabled by generating the combined image and displaying the combined image on the display 13 as described above.

For example, in a display method in which the rectangular front view image and the side view image are located side by side, a display method in which a monitor that displays the front view image and a monitor that displays the side view image are displayed side by side, or the like, the surgeon needs to largely move his or her viewpoint to view the side view images. In contrast, according to the display method of the present disclosure, the viewpoint is needless to be moved, and the positional relationship between the front view image and the side view images can be recognized promptly.

That is, according to the display method of the present disclosure, the surgeon can easily and promptly recognize the positional relationship between the front view image and the side view images, and can easily recognize not only the surgical site in the front view direction but also the operative field around the surgical site. Thus, the images that are obtained by the front view camera 21 and the side view camera 22 can be present in an easily comprehensible manner.

Also, the surrounding operative field other than the front view direction can be recognized easily, and thus the endoscope probe 11 and forceps can be prevent from contacting an organ in an area other than the front view direction, for example.

<Example of Parameter>

The parameters of the combined image that are settable by the setting unit 36 will be described with reference to FIGS. 8 to 14.

Figure 8:
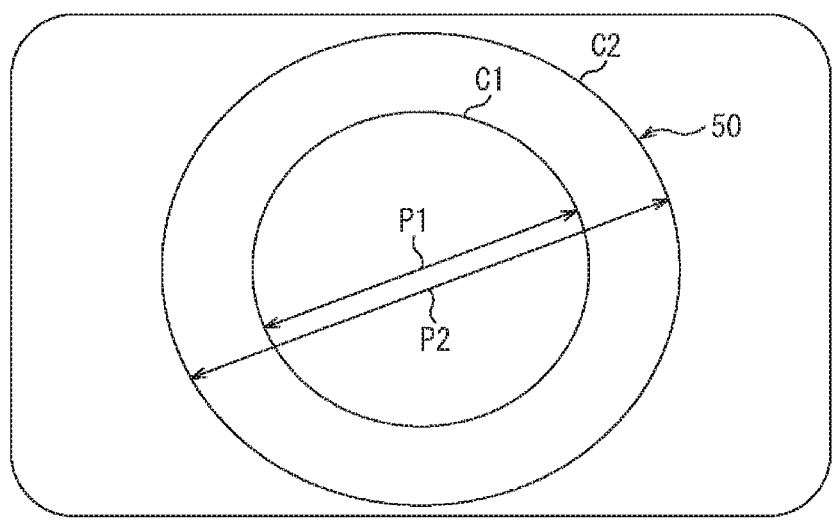
FIG. 8 is a diagram for describing settable parameters of a combined image.

The diameter P1 of the first circle C1 and the diameter P2 of the second circle C2 of the combined image 50, which are illustrated in FIG. 8 for example, can be set in the setting unit 36. The height of the side view image of the fan shape is decided, by the relationship between the diameter P1 and the diameter P2.

Figure 9:
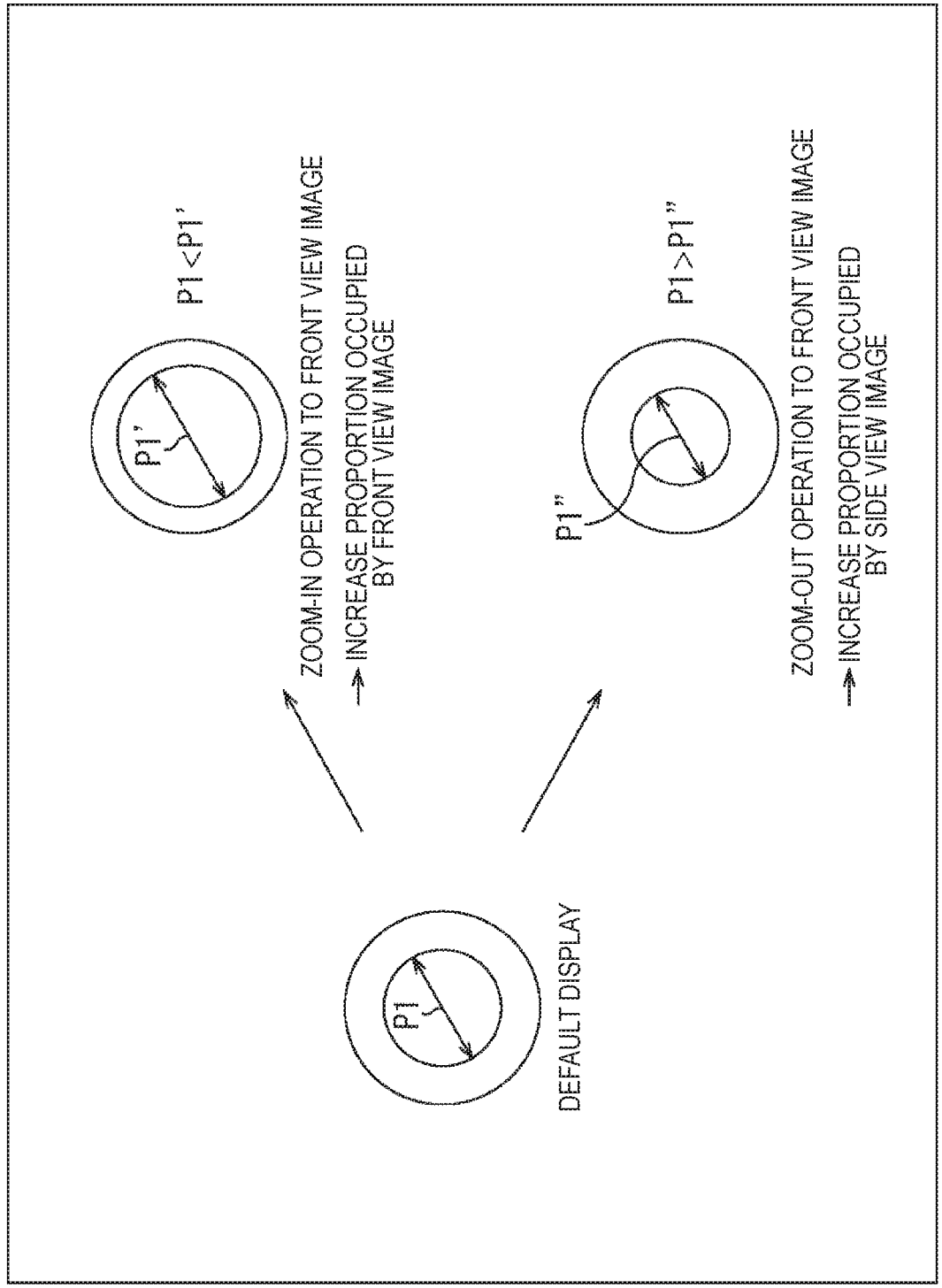
FIG. 9 is a diagram for describing parameter control according to zoom operation.

The diameter P1 of the first circle C1 and the diameter P2 of the second circle C2, which are set here, may be fixed values, and may be controlled and changed according to zoom operation to the front view image by the image combining unit 33, from a default value in an initial state, as illustrated in FIG. 9, for example.

That is, FIG. 9 illustrates an example of control that changes the diameter P1 of the first circle C1 of the combined image, according to the zoom operation.

When zoom-in operation of the front view image is performed, it is probably heavy for the user to gaze the front view image, and thus the image combining unit 33 executes a control for changing the diameter of the first circle C1 in which the front view image is displayed to a value P1' that is larger than the default value P1.

On the other hand, when zoom-out operation of the front view image is performed, it is probably important for the user to widely confirm the circumference of the front view image, and thus the image combining unit 33 executes a control for changing the diameter of the first circle C1 in which the front view image is displayed, to a value P1" that is smaller than the default value P1.

Figure 10:
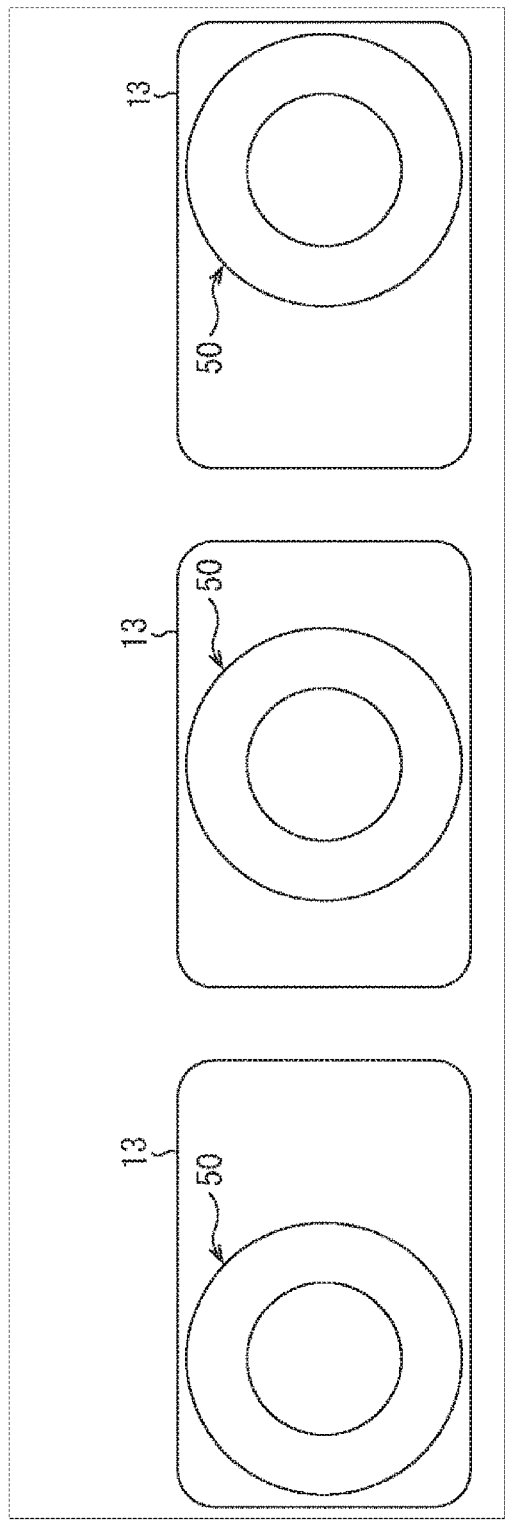
FIG. 10 is a diagram for describing settable parameters of a combined image.

Also, the setting unit 36 can set the position on the display 13 at which the combined image 50 is displayed, with a parameter, such as right side, center, and left side, as illustrated in FIG. 10, for example.

Figure 11:
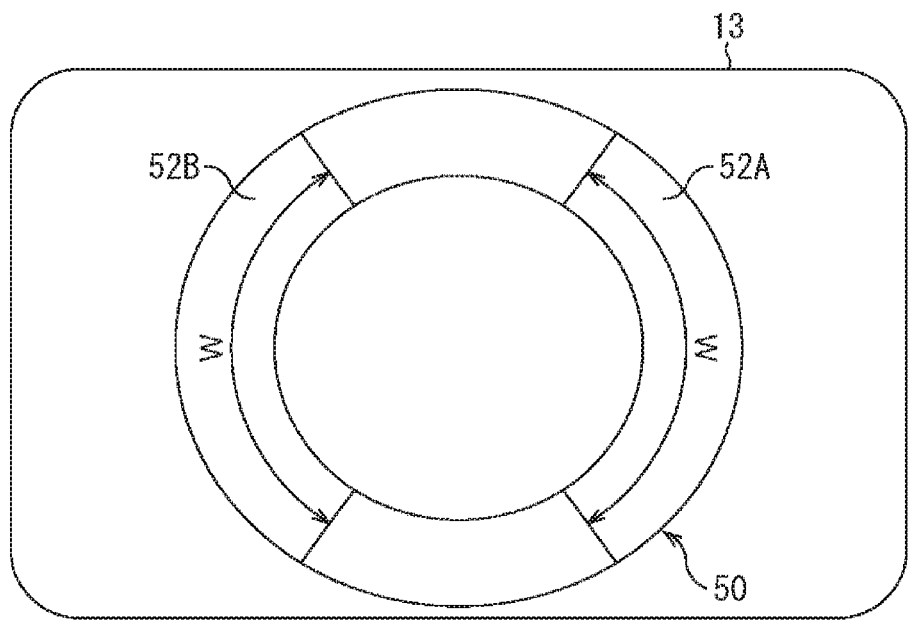
FIG. 11 is a diagram for describing settable parameters of a combined image.

Also, as illustrated in FIG. 11, lateral widths W of the fan shapes of the side view A camera display region 52A and the side view B camera display region 52B can be set.

Figure 12:
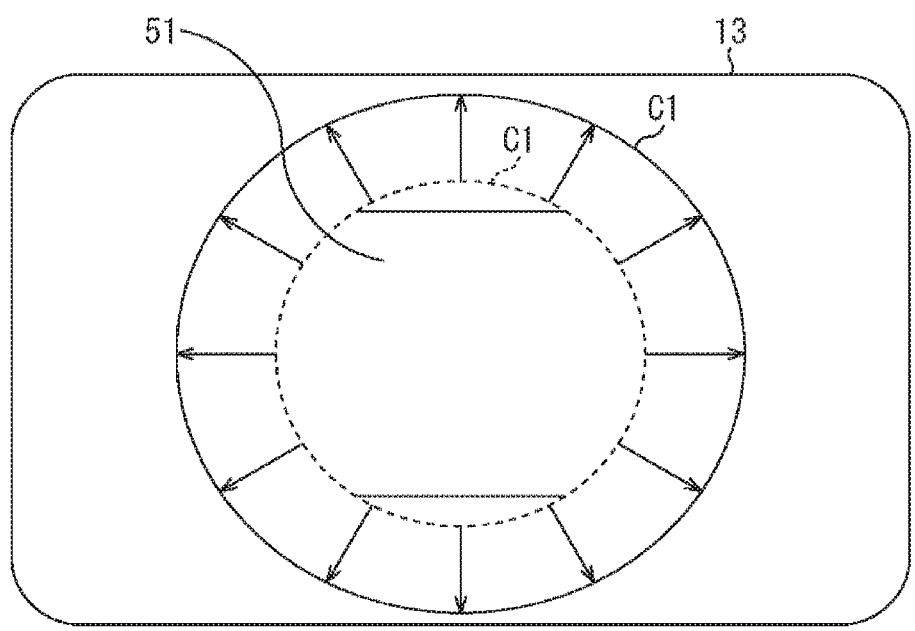
FIG. 12 is a diagram for describing settable parameters of a combined image.
Figure 13:
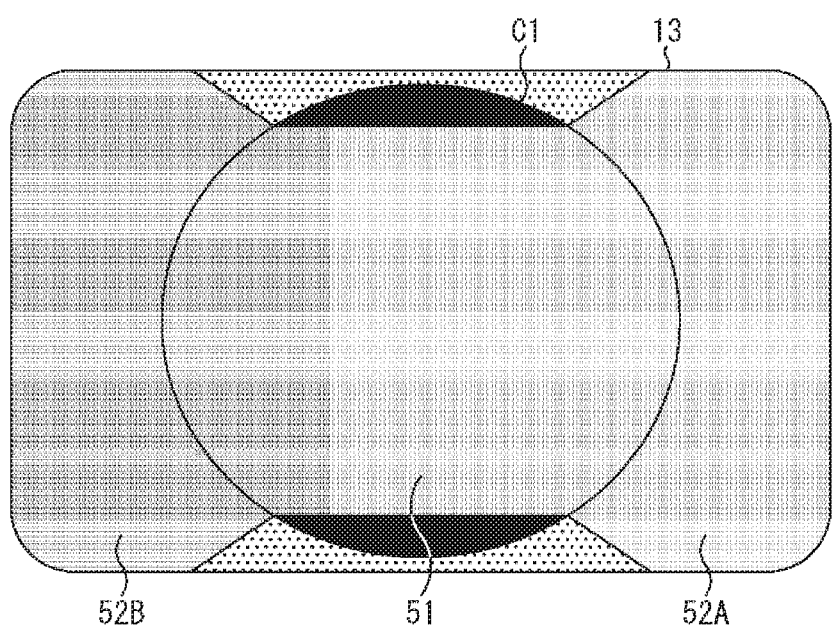
FIG. 13 is a diagram for describing settable parameters of a combined image.
Figure 14:
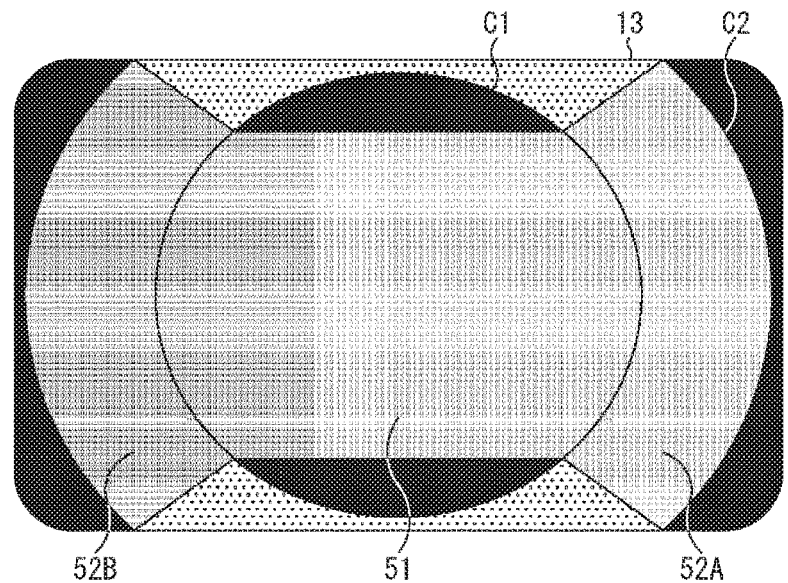
FIG. 14 is a diagram for describing settable parameters of a combined image.

A display mode in which the diameter of the first circle C1 that includes the front view image display region 51 is changed according to the zoom magnification of the front view camera 21 as illustrated in FIG. 12, a display mode in which, when the diameter of the first circle C1 is changed according to the zoom magnification, the side view A camera display region 52A and the side view B camera display region 52B that display the side view images spread out of the display region of the display 13 as illustrated in FIG. 13, a display mode in which the heights of the side view images are adjusted in such a manner that the side view A camera display region 52A and the side view B camera display region 52B do not spread out of the display region of the display 13 as illustrated in FIG. 14, or the like can be set.

Various types of display settings described above are appropriately selected according to preference of the surgeon. Note that the user is needless to set all the parameters, and the image combining unit 33 automatically adjusts the parameters, when the parameters have not been set yet.

<Process Flow of Image Combining Process>

Figure 15:
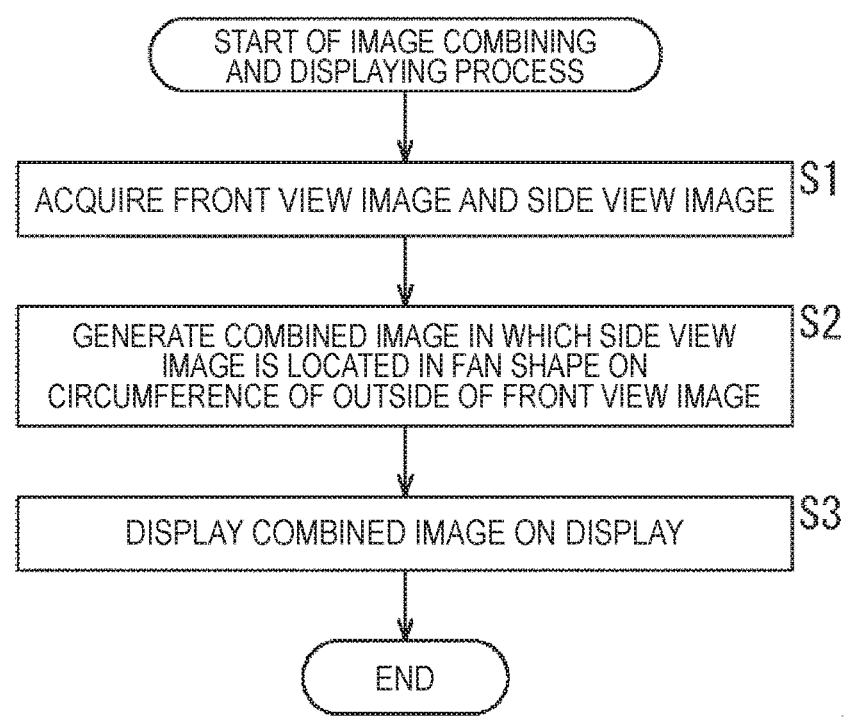
FIG. 15 is a flowchart for describing an image combining and displaying process.

The image combining and displaying process by the image processing device 12 will be described with reference to the flowchart of FIG. 15.

First, the image processing device 12 acquires the front view image and the side view image, in step S1. Specifically, the front view camera data acquisition unit 31 acquires the front view image that is supplied from the front view camera 21 and supplies the front view image to the image combining unit 33. Also, the side view camera data acquisition unit 32A acquires the side view image that is supplied from the side view camera 22A, and the side view camera data acquisition unit 32B acquires the side view image that is supplied from the side view camera 22B, and the side view camera data acquisition unit 32A and the side view camera data acquisition unit 32B supply the side view images to the image combining unit 33.

In step S2, the image combining unit 33 generates the combined image in which the front view image is located inside the first circle C1 and the side view images captured by the side view camera 22A and the side view camera 22B are located in fan shapes on the circumference outside the first circle C1 by using the acquired front view image and the side view image, and supplies the combined image to the display control unit 34.

In step S3, the display control unit 34 converts the image data of the combined image supplied from the image combining unit 33 to the image signal of the input format of the display 13, and outputs the image signal to the display 13, in order to display the combined image on the display 13.

The above process of steps S1 to S3 is continuously executed, while the front view image and the side view image are supplied from the endoscope probe 11.

The surgeon can simultaneously observe not only the surgical site in the front view direction but also a broad area that includes the side directions, by viewing the combined image displayed by the image combining and displaying process.

<Exemplary Variant 1>

In an above example, although the number of side view cameras 22 attached to the side surface of the cylindrical endoscope probe 11 is 2 in the example described above, the number of side view cameras 22 may be 1 and may be 3 or more.

Figure 16:
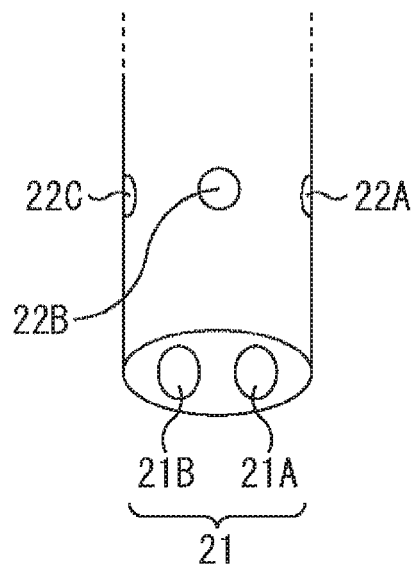
FIG. 16 is a diagram for describing a first exemplary variant.

FIG. 16 illustrates an example in which four side view cameras 22A to 22D are attached to the side surface of the endoscope probe 11 so as to capture images that divide the circumference of the side direction equally into four directions. Note that the attachment position of the side view camera 22D is at a position that is unable to be seen in FIG. 16, and thus the side view camera 22D is not illustrated in FIG. 16.

Figure 17:
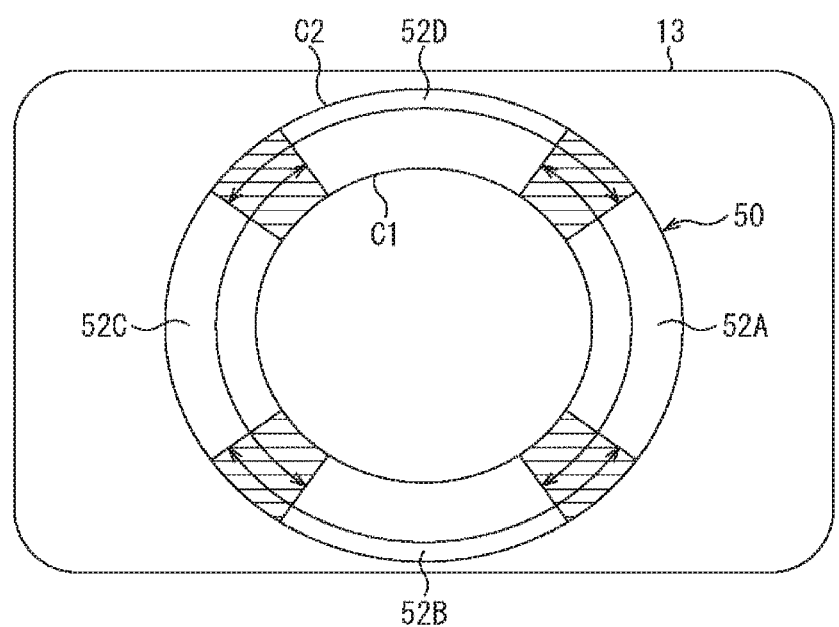
FIG. 17 is a diagram for describing the first exemplary variant.

When the four side view cameras 22A to 22D are provided, the side view A camera display region 52A, the side view B camera display region 52B, the side view C camera display region 52C, and the side view D camera display region 52D are located according to the image capturing direction, as illustrated in FIG. 17, in the region between the first circle C1 and the second circle C2.

As described above, according to the display method of the present disclosure, change of the position and the number of the side view cameras 22 can be dealt easily.

The image capturing scopes of the side view images captured by the four side view cameras 22A to 22D overlap in some cases. In the region in which the image capturing scopes overlap, a plurality of side view images that include the overlapping scopes are seamlessly connected by using an arbitrary stitching technology.

In FIG. 17, hatched regions indicate the regions in which the image capturing scopes overlap between the adjacent side view images. As the side view images in the regions in which the image capturing scopes overlap, two side view images are combined at a combination ratio α to generate a side view image of the overlapping part, in order to connect the adjacent side view images with each other, for example. Also, for example, it may be such that priority of the side view images captured by the four side view cameras 22A to 22D are set in advance, and the adjacent side view images may be connected with each other by employing one of the overlapping side view images in accordance with the set priority.

<Exemplary Variant 2>

In the above embodiment, an example has been described in which the side view cameras 22 on the side surface of the endoscope probe 11 are located equally, so that images of the entire circumference in the side direction of the endoscope probe 11 are captured as much as possible.

Figure 18:
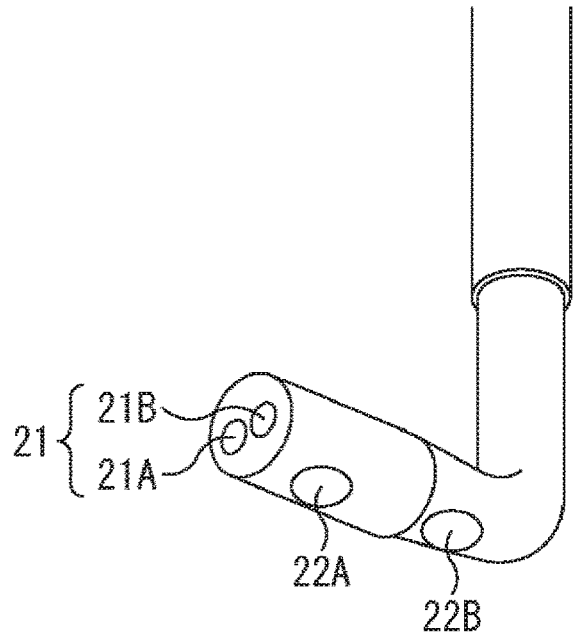
FIG. 18 is a diagram for describing a second exemplary variant.

However, as illustrated in FIG. 18, the side view cameras 22A and 22B may be located adjacent in a certain side direction only, among the circumference in the side direction of the endoscope probe 11, so that the side view cameras 22A and 22B function as stereo cameras. In this case, the two side view cameras 22A and 22B are located along the longitudinal direction of the endoscope probe 11, and thus the distance between the side view cameras 22A and 22B is long to a certain degree, and thus distance information by stereoscopic viewing can be obtained accurately.

<Exemplary Variant 3>

Figure 19:
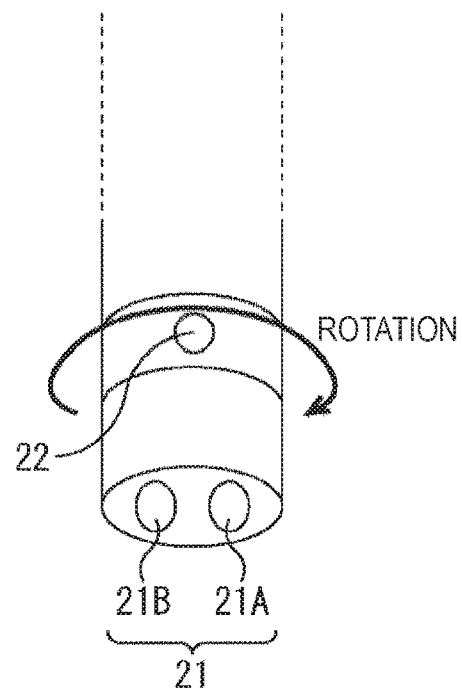
FIG. 19 is a diagram for describing a third exemplary variant.

As illustrated in FIG. 19, the endoscope probe 11 may include one side view camera 22 with a rotation mechanism, and the side view camera 22 rotates 360°, and thereby the side view image that captures the entire circumference in the side direction of the endoscope probe 11 may be acquired and displayed. In this case, the endoscope probe 11 is provided with an angle sensor that can detect the rotation angle of the side view camera 22, and the angle sensor detects the rotation angle of the side view camera 22 at a moment when the side view image is acquired. Then, the display position of the side view image in the combined image can be decided on the basis of the angle information at the moment when the side view image is acquired.

<Example of Computer Hardware Configuration>

The series of processes described above can be executed by hardware but can also be executed by software. When the series of processes is executed by software, a program that constructs such software is installed into a computer. Here, the expression "computer" includes a computer in which dedicated hardware is incorporated and a general-purpose personal computer or the like that is capable of executing various functions when various programs are installed.

Figure 20:
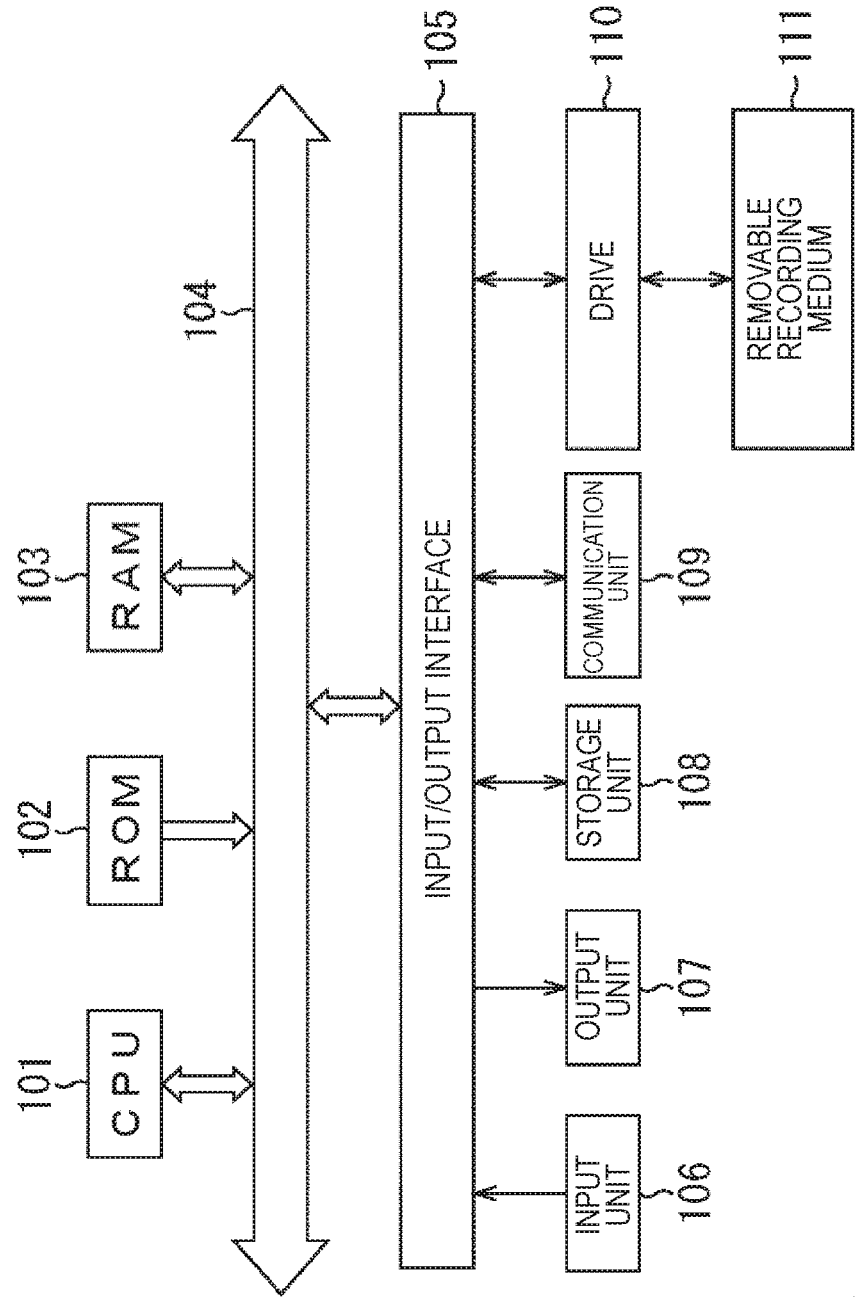
FIG. 20 is a block diagram illustrating an exemplary configuration of one embodiment of a computer according to the present disclosure.

FIG. 20 is a block diagram showing an example configuration of the hardware of a computer that executes the series of processes described earlier according to a program.

In a computer, a CPU (Central Processing Unit) 101, a ROM (Read Only Memory) 102, and a RAM (Random Access Memory) 103 are mutually connected by a bus 104.

An input/output interface 105 is also connected to the bus 104. An input unit 106, an output unit 107, a storage unit 108, a communication unit 109, and a drive 110 are connected to the input/output interface 105.

The input unit 106 is configured from a keyboard, a mouse, a microphone or the like. The output unit 107 configured from a display, a speaker or the like. The storage unit 108 is configured from a hard disk, a non-volatile memory or the like. The communication unit 109 is configured from a network interface or the like. The drive 110 drives a removable recording medium 111 such as a magnetic disk, an optical disk, a magneto-optical disk, a semiconductor memory or the like.

In the computer configured as described above, as one example the CPU 101 loads a program stored in the storage unit 108 via the input/output interface 105 and the bus 104 into the RAM 103 and executes the program to carry out the series of processes including an image combining and displaying process described earlier.

In the computer, by loading the removable recording medium 111 into the drive 110, the program can be installed into the storage unit 108 via the input/output interface 105. It is also possible to receive the program via a wired or wireless transfer medium, such as a local area network, an internet, and a digital satellite broadcast, using the communication unit 109 and install the program into the storage unit 108. As another alternative, the program can be installed in advance into the ROM 102 or the storage unit 108.

Note that the program executed by the computer may be a program in which processes are carried out in a time series in the order described in this specification or may be a program in which processes are carried out in parallel or at necessary timing, such as when the processes are called.

Further, in the present disclosure, a system has the meaning of a set of a plurality of configured elements (such as an apparatus or a module (part)), and does not take into account whether or not all the configured elements are in the same casing. Therefore, the system may be either a plurality of apparatuses, stored in separate casings and connected through a network, or a plurality of modules within a single casing.

An embodiment of the disclosure is not limited to the embodiments described above, and various changes and modifications may be made without departing from the scope of the disclosure.

For example, a form in which all or a part of the above functions are combined as appropriate can be employed.

For example, the present disclosure can adopt a configuration of cloud computing which processes by allocating and connecting one function by a plurality of apparatuses through a network.

Further, each step described by the above-mentioned flow charts can be executed by one apparatus or by allocating a plurality of apparatuses.

In addition, in the case where a plurality of processes are included in one step, the plurality of processes included in this one step can be executed by one apparatus or by sharing a plurality of apparatuses.

In addition, the effects described in the present specification are not limiting but are merely examples, and there may be additional effects.

Additionally, the present technology may also be configured as below.

(1)

An image processing device including:

an image combining unit configured to generate a combined image in which a front view image that is obtained by capturing an image of a subject in a front view direction which is a distal end direction of a probe is located in a region of a circular shape, and a side view image that is obtained by capturing an image of a subject in a side view direction which is a side direction of the probe is located in a fan shape along an outer circumference of the circular shape.

(2)

The image processing device according to (1), wherein a plurality of the side view images that are obtained by a plurality of image sensors are located in the combined image.

(3)

The image processing device according to (2), wherein a plurality of the side view images are located at positions of an outer circumference of the circular shape corresponding to positions of the plurality of image sensors of the probe.

(4)

The image processing device according to (2) or (3), wherein a plurality of the side view images that include a region in which image capturing scopes overlap are connected by stitching.

(5)

The image processing device according to any of (1) to (4), wherein continuity of video is attained at a boundary between the front view image and the side view image.

(6)

The image processing device according to any of (1) to (5), wherein the image combining unit executes a control for changing a diameter of the circular shape in which the front view image is located, according to zoom operation to the front view image.

(7)

The image processing device according to any of (1) to (6), wherein the front view image is a 3D image.

(8)

The image processing device according to any of (1) to (7), wherein the side view image is a 3D image.

(9)

The image processing device according to (8), wherein the side view image is an image that causes a feeling of being nearer as a position gets closer to an outside of the fan shape.

(10)

The image processing device according to any of (1) to (9), wherein the front view image is an image of a higher resolution than the side view image.

(11)

The image processing device according to any of (1) to (10), further including
a setting unit configured to set a display method of the combined image.

(12)
The image processing device according to (11), wherein the setting unit sets a lateral width of the side view image of the fan shape.

(13)
The image processing device according to (11) or (12), wherein
the setting unit sets a diameter of the circular shape.

(14)
The image processing device according to any of (11) to (13), wherein the setting unit sets a height of the side view image of the fan shape.

(15)
The image processing device according to any of (11) to (14), wherein
the setting unit sets a display position of the combined image in a screen.

(16)
An image processing method including:
generating, by an image processing device, a combined image in which a front view image that is obtained by capturing an image of a subject in a front view direction which is a distal end direction of a probe is located in a region of a circular shape, and a side view image that is obtained by capturing an image of a subject in a side view direction which is a side direction of the probe is located in a fan shape along an outer circumference of the circular shape.

REFERENCE SIGNS LIST 11 endoscope probe
12 image processing device
13 display
33 image combining unit
34 display control unit
35 operation unit
36 setting unit
101 CPU
102 ROM
103 RAM
106 input unit
107 output unit
108 storage unit
109 communication unit
110 drive

The invention claimed is:
1. An image processing device comprising:
processing circuitry configured to
generate a combined image based on a first image and a second image, the first image being obtained by capturing an image of a subject in a front view direction which is a distal end direction of a probe via a front view sensor, the first image being located in a predetermined region having a region size set according to zoom magnification of the first image, the second image being obtained by capturing an image of the subject in a view field direction that differs from the front view direction of the probe via a first side view sensor, and the second image being located in a fan shape along an outer circumference of the predetermined region, wherein
the fan shape has an angle equal to a view angle of the first side view sensor, and
an angle between a center position in an arc direction of the fan shape and a reference position of the first image is equal to an angle between a position of the first side view sensor and a reference position of the front view sensor.

2. The image processing device according to claim 1, wherein the predetermined region is a substantially circular region.

3. The image processing device according to claim 1, wherein the second image is captured in a direction orthogonal to the front view direction.

4. The image processing device according to claim 1, wherein the first image and the second image are endoscope images.

5. The image processing device according to claim 2, wherein a plurality of the second image that are obtained by a plurality of image sensors are located in the combined image.

6. The image processing device according to claim 5, wherein the plurality of the second image that includes regions in which image capturing scopes overlap are connected by stitching.

7. The image processing device according to claim 2, wherein continuity of video is attained at a boundary between the first image and the second image.

8. The image processing device according to claim 2, wherein the first image is a 3D image.

9. The image processing device according to claim 2, wherein the second image is a 3D image.

10. The image processing device according to claim 9, wherein the second image causes a feeling of being nearer as a position gets closer to an outside of the fan shape.

11. The image processing device according to claim 2, wherein the first image is of a higher resolution than the second image.

12. The image processing device according to claim 2, wherein the processing circuitry is further configured to set a display method of the combined image.

13. The image processing device according to claim 12, wherein the processing circuitry is further configured to set a lateral width of the second image of the fan shape.

14. The image processing device according to claim 12, wherein the processing circuitry is further configured to set a diameter of the substantially circular region.

15. The image processing device according to claim 12, wherein the processing circuitry is further configured to set a height of the second image of the fan shape.

16. The image processing device according to claim 12, wherein the processing circuitry is further configured to set a display position of the combined image in a screen.

17. The image processing device according to claim 1, wherein the first side view sensor is rotatable.

18. The image processing device according to claim 14, wherein the diameter of the substantially circular region is based on a magnification of the first image, a zoom-in operation to the first image increases a proportion of the combined image occupied by the first image, and a zoom-out operation to the first image increases a proportion of the combined image occupied by the second image.

19. An image processing method comprising:
generating, by an image processing device, a combined image based on a first image and a second image, the first image being obtained by capturing an image of a subject in a front view direction which is a distal end direction of a probe via a front view sensor, the first image being located in a predetermined region having a region size set according to zoom magnification of the first image, the second image being obtained by capturing an image of the subject in a view field direction that differs from the front view direction of the probe via a first side view sensor, and the second image being located in a fan shape along an outer circumference of the predetermined region, wherein the fan shape has an angle equal to a view angle of the first side view sensor, and an angle between a center position in an arc direction of the fan shape and a reference position of the first image is equal to an angle between a position of the first side view sensor and a reference position of the front view sensor.

20. An endoscope system comprising:

an endoscope that includes a front view sensor that captures a first image of a subject in a front view direction which is a distal end direction of a probe, and a first side view sensor that captures a second image of the subject in a view field direction that differs from the front view direction of the probe; and processing circuitry configured to generate a combined image based on the first image and the second image, the combined image being located in a predetermined region having a region size set according to zoom magnification of the first image, and the second image being located in a fan shape along an outer circumference of the predetermined region, wherein the fan shape has an angle equal to a view angle of the first side view sensor, and an angle between a center position in an arc direction of the fan shape and a reference position of the first image is equal to an angle between a position of the first side view sensor and a reference position of the front view sensor.

\* \* \* \* \*